United States Patent [19]
Zusi et al.

[11] Patent Number: 5,202,350
[45] Date of Patent: Apr. 13, 1993

[54] FURANONE ANTI-INFLAMMATORY AGENTS

[75] Inventors: F. Christopher Zusi, Tonowanda; Suresh Marathe, Amherst; William Somerville, Buffalo; Kenneth M. Tramposch, East Amherst, all of N.Y.

[73] Assignee: Bristol-Myers Squibb Co., Mew Uprl., N.Y.

[21] Appl. No.: 752,104

[22] Filed: Aug. 29, 1991

[51] Int. Cl.$^5$ .................. A61U 31/34; C07D 305/12
[52] U.S. Cl. ..................................... 514/461; 549/318
[58] Field of Search ......................... 514/461; 549/318

*Primary Examiner*—S. J. Friedman
*Attorney, Agent, or Firm*—Sandra M. Nolan

[57] ABSTRACT

New compounds (3-alkyl-5-hydroxy-3,4-dihydrofuran-2-ones) of the following general structure:

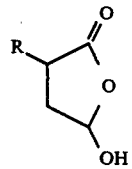

wherein R is an alkyl group or a phenylalkyl group with the alkyl moiety containing at least 6 carbon atoms, are disclosed as useful in inhibiting phospholipase $A_2$.

19 Claims, No Drawings

FURANONE ANTI-INFLAMMATORY AGENTS

BACKGROUND OF THE INVENTION

Manoalide has been described in a variety of publications:

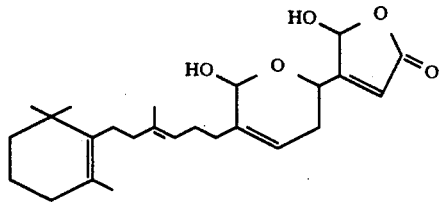

MANOALIDE

[see, for example, Glaser KB, et al., *Molecular Pharmacology*, 36:782-8 (1989)] as a phospholipase $A_2$ inhibitor. It differs from the compounds of the instant invention by containing a double bond in the furanone ring, by possessing a second, oxygen-containing ring in the side chain, and in the position of substitution of the side chain. It also has a highly complex, isoprenoid-type side chain.

U.S. Pat. No. 4,952,605 discloses several manoalide derivatives: manoalide diol (I), manoalide delta-lactone (II), manoalide delta-lactone acetate (III), dehydro-seco-manoalide (IV), luffariellolide (V), luffariellin A (VI), and luffariellin B (VII):

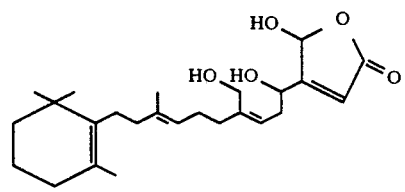
(I)

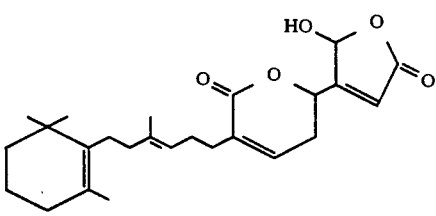
(II)

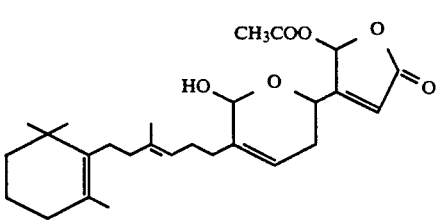
(III)

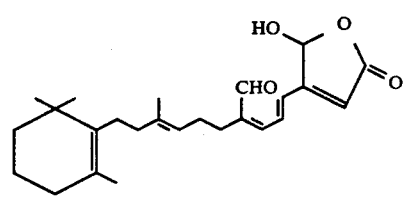
(IV)

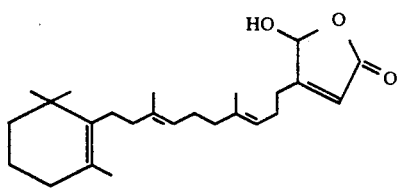
(V)

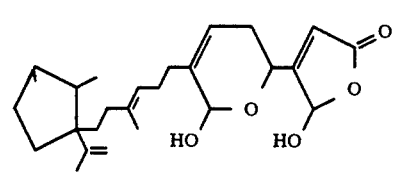
(VI)

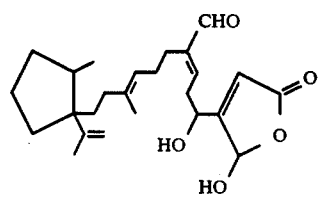
(VII)

as phospholipase $A_2$ inhibitors. All of these compounds differ from those of the instant invention in ways similar to those listed for manoalide.

In Deems R. A., et al. [*Biochim Biophys Acta* 917:258 (1987)] is disclosed HDBD:

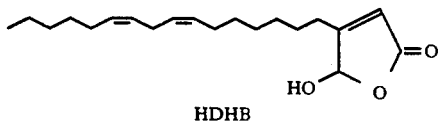

HDHB also a $PLA_2$ inhibitor. It differs from the compounds of the instant invention in the position of attachment of the side chain, by the appearance of two double bonds in the side chain, and by the presence of a double bond within the ring.

Kernan M. R., et al. [*Experimentia* 45:399 (1989)], is disclosed luffolide:

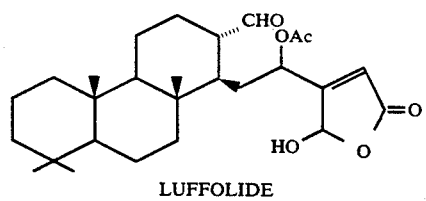

LUFFOLIDE as a $PLA_2$ inhibitor. It resembles manoalide but has an even more complicated and rigid side chain.

U.S. Pat. No. 4,874,782 discloses compounds of the following general structure as phospholipase $A_2$ inhibitors:

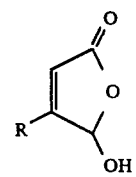

where R is a $C_8$-$C_{24}$ straight branched hydrocarbyl group optionally containing a total of 1-6 double and/or triple bonds and optionally containing an aldehyde or hydroxymethyl group, or $R^1$-L where L is a $C_2$-$C_{12}$ straight or branched hydrocarbyl linking group optionally containing 1 or 2 double or triple bonds and $R^1$ is naphthalenyloxy or benzylphenoxy. They differ from the compounds of the instant invention in the position of attachment of the side chain and in possessing a double bond within the furanone ring.

In European Patent Application 295,056 is given the general structure:

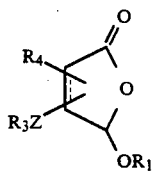

where $R^1$ is hydrogen or acyl; $R_4$ is hydrogen, bromo, or chloro; Z is —CO— or —C(OR$_2$)H—; and $R_3$ is with the proviso that $R_4$ may not be bromo or chloro when $R_3$ contains a double bond. The broken line can represent a single or double bond, although the only compounds exemplified contain a double bond.

They differ from the compounds of the instant invention in the requirement for oxygen in the side chain, by the presence (for the exemplified compounds) of a double bond in the furanone ring, and in the failure to appreciate that maximum inhibitory activity resides in a particular side chain length.

European Patent Application 369,811 discloses compounds of the following general structure as phospholipase $A_2$ inhibitors:

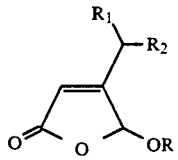

in which R is hydrogen or an acid-derived species, $R_1$ is halogen, or substituted nitrogen, oxygen, or sulfur, and $R_2$ is an alkyl group or derivative. They differ from the compounds of the instant invention in the position of attachment of the side chain to the furanone ring, in the requirement for a heteroatom in the side chain, and in the presence of a double bond in the furanone ring.

U.S. Pat. No. 4,957,917 discloses compounds of the following general structure as phospholipase $A_2$ inhibitors:

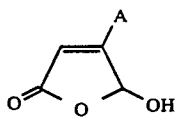

in which A is —CH(OCOR$_1$)CH$_2$CO—Y, —CH=C(R$_2$)—R (R$_2$ is halogen or COR$_5$), —CH=CH—CO—Z, —CH=C(R$_3$)—CO$_2$R, C≡C—R$_4$(-R$_4$—alkyl), —CH=CH(CH$_2$)$_n$OX, or —CH(Ph)CH$_2$CO—Y. They differ from the compounds of the instant invention in the position of attachment of the side chain, in the presence of an oxygen atom or unsaturation in the side chain, and in the occurrence of a double bond in the furanone ring.

Finally, Campbell M. M., et al. [Tetrahedron 14:4551-6 (1959)] disclosed compounds of the following general structure as PLA$_2$ inhibitors:

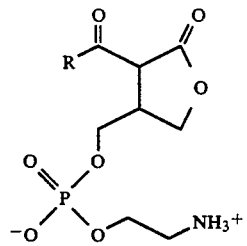

where R=propyl or arachidonoyl. They differ from the compounds of the instant invention in that they lack the 5-hydroxy group on the furanone ring, they have an aminoethylphosphate group attached at the 4-position, and they have a carbonyl group in the first position of the 3-substituent.

Phospholipase $A_2$ activity results in the liberation of fatty acids, primarily arachidonic acid, by the hydrolysis of the sn-2 position of cellular phospholipids. Both the free arachidonic acid and the lysophospholipid thus resulting can be converted by other enzymes into potent inflammatory mediators. The acid can be converted into prostanoids, leukotrienes, lipoxins, etc., while the lysophospholipid can be converted into platelet activating factor (PAF). Elevated levels of phospholipase $A_2$ have been demonstrated in several inflammatory conditions. For further discussion, a number of reviews have appeared. See for example, Mobilio D. and Marshall L. A. [*Annual Reports in Medicinal Chemistry*, Vol. 24, pg. 157 (1989)], Vadas P. and Pruzanski W. [*Laboratory Investigation*, Vol. 55:391 1986)], Hoffman G. E. and Guder W. [*Klinische Woechenschrifte*, Vol 67:149 (1989)], and Mansbach C. [*Gastroenterology*, Vol 98:1369 (1990)]. Inhibition of phospholipase $A_2$ is thus an attractive approach to the control of inflammation.

THE INVENTION

We have now discovered that 3-alkyl-5-hydroxy-4,5-dihydro-furan-2-ones of the following structure:

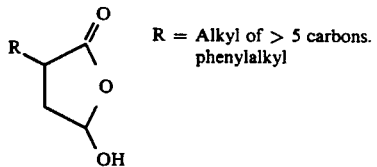

R = Alkyl of > 5 carbons. phenylalkyl wherein R=alkyl or phenylalkyl with the alkyl group containing from 6 to 20, and preferably from 6 to 16 carbon atoms, have good PLA$_2$ inhibitory activity and thus are of use for treating inflammatory conditions.

DETAILED DESCRIPTION OF THE INVENTION

The invention is concerned with the novel compounds of the invention and their use as anti-inflammatory agents, i.e., in processes and compositions for treating inflammation.

The Compounds

The compounds may exist in either an open-chain form or in a 5-membered ring form, as shown below:

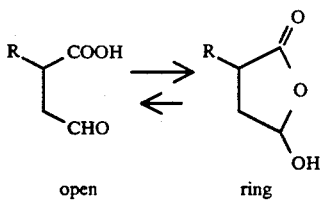

open    ring

They are predominantly in the ring form.

The compounds may conveniently be prepared as shown below:

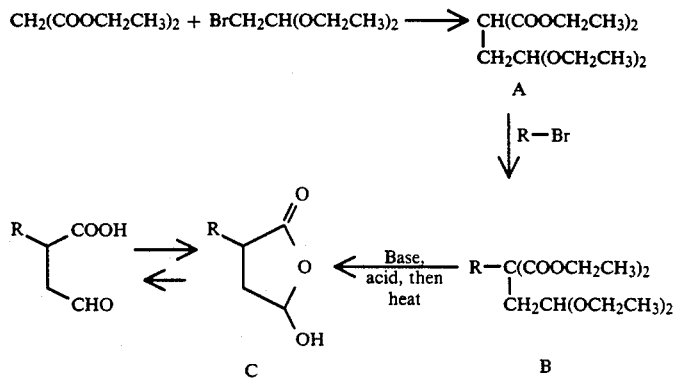

Diethyl malonate is alkylated with bromoacetaldehyde diethyl acetal to give the highly protected malonate derivative A. This is then treated with alkyl or substituted-alkyl bromides (R-Br) to give alkylated compound B. The ester groups are cleaved by base hydrolysis, then, upon acidification and heating, one of the free malonic acid carboxyls is lost as carbon dioxide, and the acetal group is hydrolyzed to the free aldehyde. As stated previously, the final compounds exist predominantly in the closed-ring form.

Alternatively, the compounds may also be synthesized as follows:

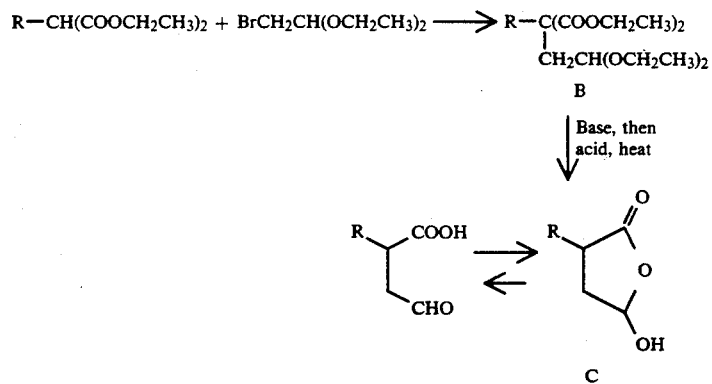

Alkyl malonates may be further alkylated with bromoacetaldehyde diethyl acetal to give B directly, which is then hydrolyzed and converted to C as described.

Compositions and Processes

The compounds are administered via oral, parenteral, topical, or other means. They are generally administered in formulations containing suitable amounts of pharmaceutical carriers and other conventional additives at intervals ranging from about 1 to about 4 times per day.

The compounds of the invention are useful in a variety of formulations and methods which employ them in suitable therapeutic amounts. It is preferred, however, that the comounds of the invention he applied via topical forhnulations. In such formulations, the active compound(s) is generally used at concentrations ranging from about 0.25 to about 10%, preferably about 2 to about 4%.

One or more of the compounds of the invention may be used alone or in combination with suitable amounts of additional therapeutic ingredient(s).

EXAMPLES

The following examples illustrate the invention.

EXAMPLE 1

Synthesis of the intermediate (2,2-Diethoxy)Ethylmalonic Acid, Diethyl Ester (A)

A mixture of 10.6 gms (0.25 moles) sodium hydride 57% oil dispersion and 75 mL hexane was stirred under argon for 10 minutes. The hexane solvent was replaced by 125 mL of dry dimethylformamide, and to this suspension was added dropwise 40.5 gms (0.25 moles) diethyl malonate over 30 minutes. 49 gms (0.25 moles) bromoacetaldehyde diethyl acetal was then added dropwise over 20 minutes. After the addition was complete, the reaction mixture was stirred at 86 degrees Celsius for 18 hours, then cooled to room temperature and diluted with 600 mL of an ice-water mixture. The mixture was 4×200 mL ether extracted. The ether extracts were combined, washed twice with 50 mL cold 5% HCl, twice with 50 mL 5% NaHCO$_3$ solution, twice with saturated NaCl solution, dried over magnesium sulfate, and filtered. The ether was evaporated in vacuo to give 55.2 gms of oil. The crude oil was purified by two successive vacuum distillations to finally give 18 gms of pure product, b.p. 81–83 degrees/0.1 mmHg. Elemental analysis: calculated C 56.51, H 8.75; found C 57.11, H 9.09.

IR (NaCl plates): Strong band from 2850–3000 cm$^{-1}$ (C—H stretch)
Strong band at 1730 cm$^{-1}$ (C=O stretch)
NMR (CDCl$_3$): d of d 4.6 (1H); C$\underline{H}$(OEt)$_2$
q 4.2 (4H); ester C$\underline{H}_2$
( m 3.6 (5H); acetal C$\underline{H}_2$ and C$\underline{H}$(COO)$_2$
t 2.2 (2H); C—C$\underline{H}_2$—C
t of d 1.2 (12H); ester and acetal C$\underline{H}_3$

EXAMPLE 2

Synthesis of the intermediate, [1-n-Decyl-2,2-Diethoxy]Ethyl Malonic Acid, Diethyl Ester (B, R=C$_{10}$)

To a stirred suspension of 1.6 gms (0.037 moles) sodium hydride 57% oil dispersion in 25 mL dimethylformamide was added 10 gms (0.036 moles) of the product from Example 1, dropwise over 20 minutes. The mixture was stirred for a further 30 minutes after complete addition, then 8.2 gms (0.037 moles) n-decyl bromide was added over 15 minutes. The reaction mixture was then heated with stirring at 86 degrees for 18 hours, then cooled to room temperature and diluted with 200 mL water. The water was 4×40 mL ether extracted, the organic phases were combined, and the combined ether extracts were twice washed with 20 mL water, twice washed with saturated NaCl solution, dried over MgSO$_4$, and filtered. The solvent was removed in vacuo and the crude oil remaining was vacuum distilled to give 8.2 gms (54.6%) of pure product, b.p. 141–3 degrees/0.01 mmHg. Elemental analysis: calculated C 66.31, H 10.65; found C 66.77, H 10.86.

IR (NaCl plates): Strong band from 2850–3000 cm$^{-1}$ (C—H stretch)
Strong band at 1730 cm$^{-1}$ (C=O stretch)
NMR (CDCl$_3$): d of d 4.4; C$\underline{H}$(OEt)$_2$
q 4.2; ester C$\underline{H}_2$
q of d 3.6; acetal C$\underline{H}_2$
d 2.2; C—C$\underline{H}$—C
m 1.9–1.0; alkyl C$\underline{H}_2$ and alkyl, acetal, and ester C$\underline{H}_3$

EXAMPLE 3

3-n-Decyl-5-Hydroxy-3,4-Dihydro-Furan-2-One (C, R=C$_{10}$)

To a stirred solution of 2.0 gms of the product from Example 2 in 20 mL ethanol was added 0.5 mL 10% aqueous NaOH solution and the mixture was stirred at room temperature for 18 hours. The solvent was removed in vacuo and the residue dissolved in water, the aqueous phase three times washed with 40 mL 3:1 hexane:ether, and the layers separated. The aqueous phase was acidified to pH 2 with hydrochloric acid and refluxed for 2 ½ hours, cooled to room temperature, then four times extracted with 50 mL ether. The ether extracts were combined, washed twice each with water and saturated NaCl solution, dried over MgSO$_4$, filtered, and the solvent evaporated in vacuo to give 0.9 gms oil. The crude oil was distilled in vacuo in a Kugelrohr apparatus to give 0.58 gms (49.8%) product, b.p. 130 degrees/0.2 mmHg.

IR (NaCl plates): Broad, weak band 3100–3600 cm$^{-1}$ (OH stretch)
Strong band from 2850–3000 cm$^{-1}$ (C—H stretch)
Strong band 1780 cm$^{-1}$ (closed ring C=O)
Medium band 1730 cm$^{-1}$ (open chain C=O)
Mass Spectrometer: Molecular ion m/e 242
Gas Chromatograph: 90% main component

EXAMPLE 4

Synthesis of [1-n-Undecyl-2,2-Diethoxy]Ethyl Malonic Acid, Diethyl Ester (B, R=C$_{11}$)

This product was obtained by the procedure of Example 2 to give 56% yield of an oil b.p. 145–7 degrees/0.05 mmHg. Elemental analysis: calculated C 66.94, H 10.77; found C 67.48, H 10.38.

IR (NaCl plates): Strong band from 2850–3000 cm$^{-1}$ (C—H stretch)
Strong band at 1730 cm$^{-1}$ (C=O stretch)
NMR (CDCl) d of d 4.4; C$\underline{H}$(OEt)$_2$
q 4.2; ester C$\underline{H}_2$
q of d 3.6; acetal C$\underline{H}_2$
d 2.2; C—C$\underline{H}_2$—C
( m 1.9–1.0; alkyl C$\underline{H}_2$ and alkyl, acetal, and ester C$\underline{H}_3$

EXAMPLE 5

3-n-Undecyl-5-Hydroxy-3,4-Dihydro-Furan-2-One (C, R=C$_{11}$)

To a stirred solution of 4.4 gms (0.01 moles) of the product from Example 4 in 30 mL ethanol was added 7 mL 14% aqueous NaOH solution, and the mixture was stirred at room temperature for 72 hours, then raised to reflux for 30 minutes. It was cooled to room temperature, then concentrated in vacuo. The residue was dissolved in 100 mL water, which was 3×60 mL extracted with 1:1 hexane:ether. The layers were separated, the aqueous layer was cooled to 5 degrees, and acidified to pH 3 with hydrochloric acid. The acidified layer was 4×50 mL ether extracted, and the ether extracts were combined, washed twice each with 20 mL water and saturated NaCl solution, then dried over MgSO$_4$ and filtered. The ether was removed in vacuo and the resulting oil was heated in an oil bath at 175 degrees for 2 hours. It was then cooled to room temperature, dissolved in 25 mL ethanol, and stirred at room temperature for 18 hours after the addition of 7 mL 14% NaOH solution. The ethanol was removed in vacuo, and the residue was dissolved in water. The aqueous solution was 3×60 mL 1:1 ether:hexane extracted and the organic layer discarded. The aqueous layer was acidified to pH 2 with hydrochloric acid and the mixture heated at 80 degrees for 1 hour. It was then cooled and 4×50 mL ether extracted. The combined ether extracts were washed twice with 20 mL water and 20 mL saturated NaCl solution, dried over MgSO$_4$, filtered, and evaporated in vacuo to give an oil. The crude product was distilled in vacuo to give 0.3 gms (12%) pure product, b.p. 130–40 degrees/0.3 mmHG. Elemental analysis: calculated C 70.27, H 11 01; found C 70.20, H 11.05.

IR (NaCl plates): Broad band 3100–3500 cm$^{-1}$ (OH stretch)
Strong band 2850–3000 cm$^{-1}$ (CH stretch)
Strong band 1780 cm$^{-1}$ (closed ring C=O)

EXAMPLE 6

Synthesis of [1-n-Dodecyl-2,2-Diethoxyl]Ethyl Malonic Acid, Diethyl Ester(B, R=C$_{12}$)

This product was obtained by the procedure of Example 2 to give 54% yield of an oil, b.p. 162–5 degrees/0.2 mmHg. Elemental analysis: calculated C 67.53, H 10.85; found C 67.17, H 11.04.

IR (NaCl plates): Strong band from 2850–3000 cm$^{-1}$ (C—H stretch)
Strong band at 1730 cm$^{-1}$ (C=O stretch)
NMR (CDCl$_3$): d of d 4.4; C$\underline{H}_2$(OEt)$_2$
q 4.2; ester C$\underline{H}_2$
q of d 3.6; acetal C$\underline{H}_2$
d 2.2; C—C$\underline{H}_2$—C
m 1.9–1.0; alkyl C$\underline{H}_2$ and alkyl, acetal, and ester C$\underline{H}_3$

EXAMPLE 7

3-n-Dodecyl-5-Hydroxy-3,4-Dihydro-Furan-2-One (C, R=C$_{12}$)

This compound was prepared according to the procedure of Example 5 in 19% yield to give an oil of b.p. 150 degrees/0.4 mmHg. Elemental analysis: calculated C 71.07, H 11.08; found C 71.33, H 10.52.

IR (NaCl plates): Broad band 3100–3500 cm$^{-1}$ (OH stretch)
Strong band 2850–3000 cm$^{-1}$ (CH stretch)
Strong band 1780 cm$^{-1}$ (closed ring C=O)
Weak band 1730 cm$^{-1}$ (open chain C=O)

EXAMPLE 8

[1-(7-Phenylheptyl-2,2-Diethoxyl]Ethyl Malonic Acid, Diethyl Ester (B, R=Ph—(CH$_2$)$_7$—)

This product was obtained by the procedure of Example 2 to give product in 58% yield as an oil of b.p. 185–90 degrees/0.25 mmHg. Elemental analysis: calculated C 69.30; H 9.40; found C 69.35, H 9.45.

IR (NaCl plates): Strong band from 2850–3000 cm$^{-1}$ (C—H stretch)
Strong band at 1730 cm$^{-1}$ (C=O stretch)
NMR (CDCl$_3$): s 7.2; phenyl $\underline{H}$
d of d 4.5; C$\underline{H}$(OEt)$_2$
q 4.2; ester C$\underline{H}_2$
q of d 3.6; acetal C$\underline{H}_2$
t 2.6; Ph—C$\underline{H}_2$
d 2.2; C—C$\underline{H}_2$—C
m 1.9–1.0; alkyl C$\underline{H}_2$ and alkyl, acetal, and ester C$\underline{H}_3$

EXAMPLE 9

3-(7-Phenylheptyl-5-Hydroxy-3,4-Dihydro-Furan-2-One (C, R=Ph—(CH$_2$)$_7$—)

This compound was prepared according to the procedure of Example 5 to give 28.5% yield of an oil, b.p. 150 degrees/0.25 mmHg. Elemental analysis: calculated C 73.88; H 8.75; found C 73.86, H 8.85.

IR (NaCl plates): Broad weak band 3150–3600 cm$^{-1}$ (OH stretch)
Strong band 2850–3000 cm$^{-1}$ (CH stretch)
Strong band 1780 cm$^{-1}$ (closed ring C=O)
Weak band 1730 cm$^{-1}$ (open chain C=O)
NMR (CDCl$_3$): s 7.3; phenyl $\underline{H}$
broad m 3.9–2.6; ring C$\underline{H}$
distorted s 1.4; alkylene C$\underline{H}_2$

EXAMPLE 10

[1-n-Amyl-2,2-Diethoxy]Ethyl Malonic Acid, Diethyl Ester (B, R=C$_5$)

To a stirred suspension of 1.4 gms (0.033 moles) sodium hydride 57% oil dispersion in 20 ml dimethylformamide was added dropwise under nitrogen 7 gms (0.03 moles) n-amyl diethyl malonate over 30 minutes. The reaction mixture was then heated to 110 degrees for 18 hours, cooled to room temperature, and diluted with 200 mL water. The aqueous layer was extracted with 4×50 mL ether, and the ether extracts were combined. They were washed twice with 20 mL water, twice with 20 mL saturated sodium chloride solution, dried over magnesium sulfate, filtered, and evaporated in vacuo to give an oil. The crude oil was vacuum distilled to give 4.5 gms (44%) pure product, b.p. 96–102 degrees at 0.05 mmHg. Elemental analysis: calculated C 62.40, H 9.89; found C 62.70, H 9.96.

IR (NaCl plates): Strong band from 2850–3000 cm$^{-1}$ (C—H stretch)
Strong band at 1730 cm$^{-1}$ (C=O stretch)
NMR (CDCl$_3$): d of d 4.6; C$\underline{H}$(OEt)$_2$
q 4.2; ester C$\underline{H}_2$
m 3.6; acetal C$\underline{H}_2$
d 2.2; C—C$\underline{H}_2$—C
m 1.9–1.0; alkyl C$\underline{H}_2$ and alkyl, acetal, and ester C$\underline{H}_3$

EXAMPLE 11

3-n-Amyl-5-Hydroxy-3,4-Dihyro-Furan-2-One (C, R=C$_5$)

3.4 gms of the product of Example 10 was dissolved in 40 mL ethyl alcohol, then was added 10 mL 10% aqueous NaOH solution. The resulting mixture was refluxed for 18 hours, cooled to room temperature, then concentrated in vacuo. The residue was dissolved in 60 mL water and washed three times with 25 mL ether.

The aqueous layer was acidified to pH 2 with hydrochloric acid and the resulting mixture was refluxed for 30 minutes and cooled to room temperature. The cooled water layer was 4×30 mL ether extracted. The ether extracts were combined, washed twice with 30 mL water, twice with 20 mL saturated NaCl solution, dried over $MgSO_4$, filtered, and the ether removed in vacuo. The crude product thus obtained was vacuum distilled to give 0.8 gms (47%) pure product, b.p. 98–106 degrees at 0.025 mmHg. Elemental analysis: calculated C 62.77%, H 9.35%; found C 62.88%, H 9.58%.

IR (NaCl plates): Broad band 3100–3600 cm$^{-1}$ (OH stretch)

Strong band from 2850–3000 cm$^{-1}$ (C—H stretch)

Strong band 1740–1800 cm$^{-1}$ (5-membered ring C=O)

EXAMPLE 12

[1-n-Hexadecyl-2,2-Diethoxy]Ethyl Malonic Acid, Diethyl Ester (B, R=$C_{16}$)

To a stirred suspension of 1.4 gms (0.03 moles) sodium hydride 57% oil dispersion in 20 mL dimethylformamide was added dropwise under nitrogen 11.5 gms (0.03 moles) diethyl n-hexadecyl malonate over 30 minutes. After stirring for a further 30 minutes, 5.9 gms (0.03 moles) bromoacetaldehyde, diethyl acetal was added dropwise over 30 minutes and the resulting mixture was heated at 110 degrees for 24 hours. The reaction mixture was further treated as described in Example 10 to give 1.9 gms of product b.p. 169–74 degrees/0.05 mmHg. Elemental analysis: calculated C 69.56, H 11.27; found C 69.78, H 11.24

IR (NaCl plates): Strong band from 2850–3000 cm$^{-1}$ (C—H stretch)

Strong band at 1730 cm$^{-1}$ (C=O stretch)

EXAMPLE 13

3-n-Hexadecyl-5-Hydroxy-3,4-Dihydro-Furan-2-One (C, R=$C_{16}$)

The product (1.9 gms) from Example 12 was dissolved in 20 mL ethanol and 1.2 gms NaOH dissolved in 10 mL water was added. The resulting mixture was refluxed for 16 hours, then concentrated in vacuo. The residue was dissolved in water and 3×40 mL extracted with 3:1 hexane:ether. The aqueous layer was then acidified with conc. hydrochloric acid, refluxed for 1 hour, cooled, and 4×50 mL ether extracted. The ether extracts were combined, washed twice with 20 mL water and twice with 20 mL saturated NaCl solution, dried over $MgSO_4$, filtered, and evaporated in vacuo. The resulting oil was heated for 1 hour at 150 degrees, then cooled. The remaining material was triturated with hexane, whereupon it solidified. The solid was filtered off and recrystallized from hexane to give 0.2 gms (16%) of product, m.p. 62–4. Elemental analysis (as 0.6 hexane inclusion complex): calculated C 74.94, H 12.36; found C 75.05, H 12.54.

IR (NaCl plates): Broad weak band 3150–3600 cm$^{-1}$ (OH stretch)

Strong band 2850–3000 cm$^{-1}$ (CH stretch)

Strong band 1780 cm$^{-1}$ (closed ring C=O)

Weak band 1700 cm$^{-1}$ (open chain C=O)

EXAMPLE 14

Inhibitory Activity toward Human Platelet Phospholipase $A_2$

The utility of the compounds of the instant invention is shown by their inhibitory activity toward human platelet phospholipase $A_2$ and their in vivo anti-inflammatory activity. The activity against human platelet phospholipase $A_2$ was determined as described below:

$PLA_2$ Inhibition Assay

The method used is similar to that reported by Franson, et al. [Jesse R. L. and Franson R. C., *Biochim Biophys Acta* 575:467–470 (1979), Franson R. C., Patriarca P., and Elsback P., *J Lipid Res* 15:380–388 (1974)]. The enzyme was isolated from human platelets. The substrate used consisted of $^{14}$C-oleate labeled *Escherichia coli* membranes. *E. coli* cells were grown in the presence of $^{14}$C-oleic acid and then autoclaved to prepare the membranes.

Various concentrations of test compounds are preincubated with $PLA_2$ (3.6 μg/ml in a buffer consisting of 25 mM HEPES (pH 7), 150 mM NaCl, 5.0 mM $CaCl_2$, and 10% DMSO (v/v, test compound solvent) at 37° C. for 7 minutes. The *E. coli* membrane substrate is then added (0.1 mM phospholipid, 0.005 μCi $^{14}$C) and the reaction is then incubated at 37° C. for 30 minutes. The reaction is terminated by the addition of 1.9 ml tetrahydrofuran (THF), and the entire solution is applied to a solid-phase extraction column (aminopropyl resin, Analytichem). The column is rinsed with an additional 1 ml of THF. The free fatty acid product of the reaction is then eluted from the column with 1 ml of 2% acetic acid (v/v) in THF and collected in a scintillation vial. The amount of free fatty acid product is determined by liquid scintillation counting. The amount of inhibition produced by the test compound is calculated by comparing the counts obtained in the presence of the compound to those obtained in its absence (solvent only). Background counts were determined by performing incubations in the absence of enzyme.

Percent inhibition is determined by the equation:

$$\% \text{ Inhibition} = \frac{(CPM \text{ with test compound}) - (\text{background})}{(CPM \text{ without test compound}) - (\text{background})} \times 100.$$

$IC_{50}$ values (the concentration of inhibitor required to produce 50% inhibition) were determined by linear regression analysis of a plot of % inhibition versus log test compound concentration. $IC_{50}$ values for selected compounds are reported in Table 1. The data demonstrate that these compounds dose-dependently inhibit $PLA_2$.

TABLE 1

| Compound | $IC_{50}$ (mM) |
|---|---|
| Example 3 | 525 |
| Example 5 | 17 |
| Example 7 | 18 |
| Example 9 | 379 |
| Example 11 | >500 |
| Example 13 | 59 |

The table demonstrates that compounds in this series, especially those with longer side chains, have good enzyme inhibitory activity.

EXAMPLE 15

In vivo Anti-inflammatory Activity Inhibition of Phorbol-Ester-Induced inflammation The method used is similar to that reported by Young, et al. [Young J. M., Wagner B. M., Spires D. A., *J Invest Dermatol*, 80:48–52(1983); DeYound L. M., Kheifets J. B., Ballaron S. J., Young J. M., *Agents Actions* 26:335–341 (1989)]. An inflammatory reaction is induced by the topical application of 0.01% (w/v) tissue plasminogen activator (TPA) to the ears of CD-1 mice. An acute inflammatory reaction is produced, resulting in ear edema. TPA, with and without various concentrations of test compound, was applied to the inner and outer aspects of the ear surface (10 μl/surface). After six hours, the mice were sacrificed and the ears removed. Ear tissue punches (5/16″) were taken from each ear and weighed to measure edema.

The anti-inflammatory activity of the test compounds was determined by comparing the edema produced by TPA without test compound to that produced in its presence.

Percent inhibition values were determined by the equation:

$$\% \text{ Inhibition} = \frac{(TPA \text{ with test compound group}) - (\text{untreated group})}{(TPA \text{ without test compound group}) - (\text{untreated group})} \times 100.$$

The data for these compounds are shown in Table 2. These compounds effectively block edema in this assay.

TABLE 2

| Compound | Dose (w/v) | % Inhibition of Ear Edema |
| --- | --- | --- |
| Example 5 | 2.6% | 34.6 |
| Example 13 | 10% | 45 |
| Example 13 | 7.5% | 33.5 |
| Example 13 | 5.0% | 24.6 |
| Example 13 | 2.5% | 6.8 |

Table 2 shows that the compounds tested effectively blocked edema in this assay.

Reasonable variations, such as those which would occur to a skilled artisan, can be made herein without departing from the scope of the invention.

We claim:

1. A compound of the following structure:

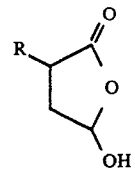

wherein R is a straight alkyl group containing at least 6 carbons, or phenylalkyl wherein the alkyl chain contains at least 6 carbons.

2. The compound 3-n-decyl-5-hydroxy-3,4-dihydrofuran-2-one.

3. The compound 3-n-undecyl-5-hydroxy-3,4-dihydrofuran-2-one.

4. The compound 3-n-dodecyl-5-hydroxy-3,4-dihydrofuran-2-one.

5. The compound 3-n-hexadecyl-5-hydroxy-3,4-dihydrofuran-2-one.

6. The compound 3-(7-phenylheptyl)-5-hydroxy-3,4-dihydrofuran-2-one.

7. A method of treating an inflammation comprising administering to a patient a formulation containing a therapeutic amount of the compound of claim 1.

8. The method of claim 7 wherein the compound is 3-n-decyl-5-hydroxy-3,4-dihydrofuran-2-one.

9. The method of claim 7 wherein the compound is 3-n-undecyl-5-hydroxy-3,4-dihydrofuran-2-one.

10. The method of claim 7 wherein the compound is 3-n-dodecyl-5-hydroxy-3,4-dihydrofuran-2-one.

11. The method of claim 7 wherein the compound is 3-n-hexadecyl-5-hydroxy-3,4-dihydrofuran-2-one.

12. The method of claim 7 wherein the compound is 3(7-phenylheptyl)-5-hydroxy-3,4-dihydrofuran-2one.

13. An anti-inflammatory composition containing an effective amount of the compound of claim 1 and a pharmaceutical carrier.

14. An anti-inflammatory composition containing an effective amount of the compound of claim 2 and a pharmaceutical carrier.

15. An anti-inflammatory composition containing an effective amount of the compound of claim 3 and a pharmaceutical carrier.

16. An anti-inflammatory composition containing an effective amount of the compound of claim 4 and a pharmaceutical carrier.

17. An anti-inflammatory composition containing an effective amount of the compound of claim 5 and a pharmaceutical carrier.

18. An anti-inflammatory composition containing an effective amount of the compound of claim 6 and a pharmaceutical carrier.

19. The composition of claim 13 containing from about 0.25 to about 10% of the compound.

* * * * *